United States Patent
Gai et al.

(10) Patent No.: US 12,280,076 B2
(45) Date of Patent: Apr. 22, 2025

(54) **USE OF *RHODOCOCCUS RUBER* CELL WALL SKELETON IN REGENERATIVE MEDICINE**

(71) Applicant: LIAONING GREATEST BIO-PHARMACEUTICAL CO., LTD., Benxi (CN)

(72) Inventors: Bo Gai, Benxi (CN); Chunyan Dou, Benxi (CN); Peisheng Jin, Benxi (CN); Yi Zhang, Benxi (CN); Guoying Zhang, Benxi (CN)

(73) Assignee: LIAONING GREATEST BIO-PHARMACEUTICAL CO., LTD., Benxi (CN)

( * ) Notice: Subject to any disclaimer, the term of this patent is extended or adjusted under 35 U.S.C. 154(b) by 528 days.

(21) Appl. No.: 17/792,396

(22) PCT Filed: Jan. 20, 2021

(86) PCT No.: PCT/CN2021/072871
§ 371 (c)(1),
(2) Date: Jul. 12, 2022

(87) PCT Pub. No.: WO2021/147899
PCT Pub. Date: Jul. 29, 2021

(65) Prior Publication Data
US 2023/0069441 A1 Mar. 2, 2023

(30) Foreign Application Priority Data
Jan. 21, 2020 (CN) .......................... 202010068249.1

(51) Int. Cl.
| | | |
|---|---|---|
| *A61K 35/28* | (2015.01) | |
| *A61K 35/545* | (2015.01) | |
| *A61K 35/74* | (2015.01) | |
| *A61P 17/02* | (2006.01) | |
| *C12N 1/20* | (2006.01) | |
| *C12R 1/01* | (2006.01) | |

(52) U.S. Cl.
CPC ............ *A61K 35/28* (2013.01); *A61K 35/545* (2013.01); *A61K 35/74* (2013.01); *A61P 17/02* (2018.01); *C12N 1/205* (2021.05); *C12R 2001/01* (2021.05)

(58) Field of Classification Search
CPC ...... A61K 35/28; A61K 35/545; A61K 35/30; A61K 35/34–35; A61K 35/50–51; C12N 5/0667; C12N 5/0603–0608; C12N 5/0623; C12N 5/0528; C12N 5/066; C12N 5/063; C12N 5/0662–0669; C12N 5/0672; C12N 5/0689; C12N 5/0692; C12N 5/0695; C12N 5/0696
See application file for complete search history.

(56) References Cited

FOREIGN PATENT DOCUMENTS

| | | |
|---|---|---|
| CN | 102071141 A | 5/2011 |
| CN | 108795859 A | 11/2018 |
| CN | 108815197 A | 11/2018 |
| CN | 108815198 A | 11/2018 |
| EP | 1 547 607 A1 | 6/2005 |
| EP | 1 741 438 A1 | 1/2007 |

OTHER PUBLICATIONS

Gein, Sergey et al., "In vitro cytokine stimulation assay for glycolipid biosurfactant from Rhodococcus ruber: Role of monocyte adhesion", Cytotechnology, 63:559-566 (2011).

Fiedler, Tomas et al., "Impact of bacteria and bacterial components on osteogenic and adipogenic differentiation of adipose-derived mesenchymal stem cells", 319(18):2883-2892 (Nov. 1, 2013).

*Primary Examiner* — Thane Underdahl
(74) *Attorney, Agent, or Firm* — Rodney J. Fuller; Booth Udall Fuller, PLC

(57) ABSTRACT

Provided is a use of *Rhodococcus ruber* cell wall skeleton in promoting the proliferation of stem cells, promoting the growth of stem cells, promoting the differentiation of stem cells, promoting the migration of stem cells, and improving the survival rate of stem cells; the stem cells are selected from: adult stem cells, iPSCs, and mesenchymal stem cells.

17 Claims, 4 Drawing Sheets

USE OF *RHODOCOCCUS RUBER* CELL WALL SKELETON IN REGENERATIVE MEDICINE

CROSS REFERENCE TO RELATED APPLICATIONS

The present application is the U.S. National Stage of International Application No. PCT/CN2021/072871, filed on Jan. 20, 2021, which claims the priority of Chinese patent application No. CN 202010068249.1 filed on Jan. 21, 2020, the contents of each of which are incorporated herein by reference in their entireties.
Biological Deposit of *Rhodococcus Ruber* Accession No. 17431

A Biological Deposit of *Rhodococcus Ruber* Accession No. 17431 was made at the China General Microbiological Culture Collection Center (CGMCC) (Yard No. 1(3) West Beichen Road, Chaoyang District, Beijing, Institute of Microbiology, Chinese Academy of Sciences; postal code: 100101), on Mar. 22, 2019, under the provisions of the Budapest Treaty, and assigned by the International Depositary Authority the accession number 17431. Upon issuance of a patent, all restrictions upon the Deposit will be irrevocably removed, and the Deposit is intended to meet the requirements of 37 CFR §§ 1.801-1.809. The Deposit will be maintained in the depository for a period of 30 years, or 5 years after the last request, or for the effective, enforceable life of the patent, whichever is longer, and will be replaced, if necessary, during that period; and the requirements of 37 CFR §§ 1.801-1.809 are met.

FIELD OF THE INVENTION

The present application relates to the field of regenerative medicine. Specifically, it relates to a use of *Rhodococcus ruber* (especially the cell wall skeleton) in promoting the proliferation of stem cells and promoting the differentiation of stem cells.

BACKGROUND OF THE INVENTION

Stem cells are primitive cells with self-renewal ability and multi-directional differentiation potential. Under certain conditions, they can proliferate and differentiate into different functional cells. Therefore, stem cell plays a very important role in the renewal and damage repair of various tissues and organs of living organisms, and has become the hope of many incurable diseases, especially diseases with cell and tissue loss or damage.

Stem cells include embryonic stem cells and adult stem cells. The application of embryonic stem cells are greatly limited due to ethical issues; meanwhile, adult stem cells can differentiate into functional cells and tissues, providing a basis for the wide application of stem cells; providing a new cell source for cell replacement therapy for many diseases. Therefore, adult stem cells have become the focus of research.

However, the number of stem cells in normal adult mammals is small, and the differentiation is affected by a variety of intrinsic mechanisms and microenvironmental factors; and long-term culture (especially serum-free expansion culture) of these cells in large quantities in vitro is very difficult, making these cells unsuitable for practical treatment.

Many diseases can be traced back to the loss or damage of functional cells, and cell replacement therapy is an effective treatment for these diseases. Stem cell related drugs can prevent and treat diseases caused by cell loss or damage by regulating the proliferation and differentiation of stem cells in living organisms. Stem cell related drugs are used to regulate the proliferation and directed differentiation potential of autologous stem cells, so as to reconstruct damaged functional cells and restore their biological functions.

Adipose-derived mesenchymal stem cells (Ad-MSCs) are adult stem cells derived from adipose tissue stroma with considerable self-renewal capacity and can differentiate into various types of functional cells. Evidence has shown that Ad-MSCs have great potential in stem cell-based chronic wound therapies. However, a significant obstacle to the successful use of Ad-MSCs in potential cell therapies is the viability ratio of cells after transplantation. When cells are transplanted into damaged skin tissue, they experience adverse conditions including hypoxia, inflammation, oxidative stress or others, which inevitably lead to poor survival of seeded cells after transplantation, interfering with the therapeutic effect of Ad-MSCs.

*Rhodococcus ruber* is a gram-positive bacterium. Generally speaking, its colony is orange-yellow or orange-red in color, and round in shape; the size of the colony is about 1 mm to 2 mm; the cells are spherical or short rod-shaped; it can form primary branched mycelium; and it has no flagella. *Rhodococcus ruber* is aerobic and chemically heterotrophic.

At present, researchers have performed whole gene sequencing for *Rhodococcus ruber*. For example, Fan Xin et al. performed whole gene sequencing for *Rhodococcus ruber* SD3 strain and performed bio-informatic analysis. The length of the whole genome of SD3 strain is about 5.37 Mb, the GC content is about 70.63%, and the GenBank accession number is CP029146 (Fan Xin, Whole-genome sequencing and expression analysis of heat shocking protein Dnak from *Rhodococcus ruber* SD3, Genomics and Applied Biology, January 2019).

The genus *Rhodococcus* can adapt to a variety of living environments due to its strong tolerance to organic substances and its wide degradation spectrum. Therefore, *Rhodococcus* is widely used in the fields of pollution remediation, organic compound degradation, sewage treatment and the like. At present, the main application field of *Rhodococcus ruber* lies in environmental management, see CN108862590A, CN107151635A, CN102250796A, CN1519312A, CN103627653A, CN101033454A, CN108130288A, CN104830738A, CN101619299A, CN103509833A, CN106434466A, CN101580808A, CN102604875A, CN103160491A, CN106591168A, CN106591172A and CN105820982A.

CN109576180A discloses a bacterium RDC-01 screened from the red soil in the suburbs near Panyu District, Guangzhou. The strain was identified as *Rhodococcus ruber* by 16S rRNA gene sequence analysis and cultivation characteristics identification. After inactivation, the bacterium was added as an immune adjuvant to an inactivated vaccine for animals, and it was found to be able to promote the production of antibodies in animals. However, the application of *Rhodococcus ruber* in the field of human medicine has not yet been reported.

Therefore, finding active components that specifically regulate the proliferation and differentiation of adult stem cells is a research focus of stem cell related drugs.

SUMMARY OF THE INVENTION

The present application provides an active component for the regulation of stem cells and the application thereof.

According to some embodiments of the present disclosure, provided is an isolated *Rhodococcus ruber*.

According to some particular embodiments of the present disclosure, provided is a *Rhodococcus ruber*, which was deposited at China General Microbiological Culture Collection Center (CGMCC) on Mar. 22, 2019 (Yard No. 1(3), West Beichen Road, Chaoyang District, Beijing, Institute of Microbiology, Chinese Academy of Sciences; postal code: 100101), under deposit number CGMCC No. 17431. The deposit meets the requirements of the Budapest Treaty on the International Recognition of the Deposit of Microorganisms for the Purposes of Patent Procedure.

According to some embodiments of the present disclosure, provided are a *Rhodococcus ruber* and a derivative product thereof. The derivative product is derived from *Rhodococcus ruber* and comprises the components of *Rhodococcus ruber* (such as proteins, nucleic acids, lipids, cell walls and components thereof, carbohydrates or metabolites).

In particular embodiments, provided is an isolated *Rhodococcus ruber* cell wall.

In particular embodiments, provided is an isolated *Rhodococcus ruber* cell wall, the *Rhodococcus ruber* refers to the strain under the deposit number CGMCC No. 17431.

In particular embodiments, provided is a product derived from *Rhodococcus ruber* cell wall.

In particular embodiments, provided is an isolated *Rhodococcus ruber* cell wall skeleton.

In particular embodiments, provided is an isolated *Rhodococcus ruber* cell wall skeleton, the *Rhodococcus ruber* refers to the strain under the deposit number CGMCC No. 17431.

According to some embodiments of the present disclosure, provided is a pharmaceutical composition comprising the *Rhodococcus ruber* cell wall or *Rhodococcus ruber* cell wall skeleton according to the present disclosure.

According to some embodiments of the present disclosure, provided is a product derived from *Rhodococcus ruber* cell wall, which comprises a product obtained by disruption of *Rhodococcus ruber*.

According to some other embodiments of the present disclosure, provided is a product derived from *Rhodococcus ruber* cell wall, which comprises a product obtained by disruption and purification (removing lipids, nucleic acids and proteins) of *Rhodococcus ruber*.

According to some other embodiments of the present disclosure, provided is a product derived from *Rhodococcus ruber* cell wall, which comprises *Rhodococcus ruber* cell wall.

According to some other embodiments of the present disclosure, provided is a product derived from *Rhodococcus ruber* cell wall, which comprises *Rhodococcus ruber* cell wall skeleton.

According to some embodiments of the present disclosure, provided is a pharmaceutical composition or a medical device, which comprises a product derived from *Rhodococcus ruber* cell wall.

According to some other embodiments of the present disclosure, provided is a pharmaceutical composition or a medical device, which comprises a product obtained by disruption and purification (removing lipids, and/or nucleic acids, and/or proteins) of *Rhodococcus ruber*.

According to some other embodiments of the present disclosure, provided is a pharmaceutical composition or a medical device, which comprises *Rhodococcus ruber* cell wall.

According to some other embodiments of the present disclosure, provided is a pharmaceutical composition or a medical device, which comprises *Rhodococcus ruber* cell wall skeleton.

According to some other embodiments of the present disclosure, provided is a pharmaceutical composition or a medical device, which comprises the above-mentioned product derived from *Rhodococcus ruber* cell wall.

In particular embodiments, the pharmaceutical composition further comprises a pharmaceutically acceptable excipient.

In some embodiments of the pharmaceutical composition, the product derived from *Rhodococcus ruber* cell wall is 1 part by weight, and the pharmaceutically acceptable excipient is 50 to 5000 parts by weight (for example, 50, 100, 200, 210, 220, 230, 240, 250, 260, 270, 280, 290, 300, 500, 600, 700, 1000, 1500, 2000, 2500, 3000, 3500, 4000, 4500, 5000 and any value within the range between any two values above).

In some other embodiments of the pharmaceutical composition, the *Rhodococcus ruber* cell wall is 1 part by weight, and the pharmaceutically acceptable excipient is 50 to 5000 parts by weight (for example, 50, 100, 200, 210, 220, 230, 240, 250, 260, 270, 280, 290, 300, 500, 600, 700, 1000, 1500, 2000, 2500, 3000, 3500, 4000, 4500, 5000 and any value within the range between any two values above).

In still other embodiments of the pharmaceutical composition, the *Rhodococcus ruber* cell wall skeleton is 1 part by weight, and the pharmaceutically acceptable excipient is 50 to 5000 parts by weight (for example, 50, 100, 200, 210, 220, 230, 240, 250, 260, 270, 280, 290, 300, 500, 600, 700, 1000, 1500, 2000, 2500, 3000, 3500, 4000, 4500, 5000 and any value within the range between any two values above).

In some embodiments, the pharmaceutical composition can be formulated into a liquid (liquid formulation).

In some other embodiments, the pharmaceutical composition can be formulated into a solid (powder formulation or lyophilized powder formulation).

The skilled person understands that, for the pharmaceutical composition of the present disclosure, the liquid formulation and the powder formulation (or lyophilized powder formulation) can be converted into each other, and the difference lies only in the water content. The powder formulation (or lyophilized powder formulation) is obtained by removing most or all water from the liquid formulation. The liquid formulation is obtained by dissolving (or reconstituting) the powder formulation (or lyophilized powder formulation).

In some embodiments, the medicament or pharmaceutical composition is formulated into a dosage form selected from the following group consisting of ointment, cream, emulsion, suspension, paste, gel, lotion, tincture, salve, tablet, aerosol, spray, liniment and powder; wherein, the ointment is selected from the group consisting of soft ointment, plaster and cream.

In some embodiments, the pharmaceutically acceptable excipient relates to, but is not limited to: filler, stabilizer, flavoring agent, disintegrant, binder and lubricant.

In some embodiments, the pharmaceutically acceptable excipient is for example but not limited to: dextran, lactose, microcrystalline cellulose, trehalose, glycine, xylitol, sodium carboxymethyl cellulose, erythritol, gelatin, magnesium stearate, propellant, humectant, solvent, solubilizer, emulsifier, antioxidant, pH regulator and preservative. Specifically, non-limiting examples also include: white vaseline, carbomer, hydroxypropyl methylcellulose, methyl cellulose, sodium hydroxymethyl cellulose, chitosan, sucralfate chitosan, polyvinylpyrrolidone, polyvinyl alcohol, sodium hyaluronate, dimethyl ether, tetrafluoroethane, hydrofluoroalkane, glycerin, propylene glycol, deionized water, water for injection, distilled water, ethanol, hexadecanol, octadecanol, p-aminobenzoic acid, acetamide, isopropanol, Tween, polyoxyethyl hydrogenated castor oil, stearic acid, glyceryl monostearate, triglycerol monostearate, sucrose fatty acid ester, sucrose ester, sucrose acetate isobutyrate, sorbitan tristearate, isopropyl myristate, cholesterol, squalene, squalane, n-butanol, ethylene glycol, ethanol, propylene glycol, polyglycerol ester, sulfite, cysteine, di-tert-butyl hydroxytoluene, potassium sorbate, phosphate buffer solution, triethanolamine, sodium hydroxide, ethylenediamine, laurylamine, sodium bicarbonate, hydrochloric acid, nipagins, thimerosal, chlorocresol, trichlorobutanol, benzoic acid and sodium salt thereof.

According to some embodiments of the present disclosure, provided is a method for the preparation of a product derived from *Rhodococcus ruber* cell wall, which comprises or consists of the following steps:
1) providing a *Rhodococcus ruber*;
2) optionally, culturing the *Rhodococcus ruber*;
3) optionally, collecting the cultured *Rhodococcus ruber*;
4) disrupting the cultured *Rhodococcus ruber* to obtain a disrupted product;
5.1) optionally, performing the operation of removing lipids from the disrupted product;
5.2) optionally, performing the operation of removing nucleic acids from the disrupted product;
5.3) optionally, performing the operation of removing proteins from the disrupted product;
5.4) obtaining a purified product;
6) optionally, removing water from the purified product, preferably removing water from the purified product by lyophilization;
7) optionally, aliquoting;
8) obtaining the product derived from *Rhodococcus ruber* cell wall;
wherein, steps 5.1), 5.2) and 5.3) are interchangeable in order or performed in parallel; step 6) and step 7) are interchangeable in order.

Optionally, step 5) can further include a step of removing cell membrane (for example by using a non-ionic surfactant).

Culture of *Rhodococcus ruber* is not limited to particular culture medium and culture parameters. The skilled person can use well-known and appropriate methods for culture, and can use petri dishes, culture flasks and fermenters according to the preparation scale.

For the disruption of *Rhodococcus ruber*, the purpose is to remove the substances inside the cells. Therefore, ultrasonication, lysozyme and other technologies can be used. The skilled person understands that any known or future method suitable for disrupting gram-positive bacteria is suitable for the technical solution of the present disclosure. The skilled person has the ability to adjust the particular parameters and instruments for culture, disruption, separation, collection, removal of impurity, and aliquoting according to the subsequent application (for example oral administration, injection, topical application, etc.) of the active component (the cell wall and components thereof), so as to avoid introducing factors that affect subsequent applications in the preparation steps.

In some embodiments, an organic solvent is used to remove lipids from the disrupted product. In some embodiments, a nuclease is used to remove DNA and RNA from the disrupted product. In some embodiments, a hydrolase is used to degrade proteins in the disrupted product. In some embodiments, a surfactant is used to remove cell membranes from the disrupted product.

In some embodiments, the average particle size of disruption is 10 nm to 1000 nm; mention may be made of 10, 20, 30, 40, 50, 60, 70, 80, 90, 100, 110, 120, 130, 140, 150, 160, 170, 180, 190 nm±10 nm, and the ranges between any two of the above values. There are many methods for measuring the particle size (Hu Songqing et al., Modern technology of particle size measurement, Modern Chemical Industry, 2002, 22:1).

In some particular embodiments, the average particle size of disruption is 10 nm to 800 nm.

In some other particular embodiments, the average particle size of disruption is 10 nm to 500 nm.

In some particular embodiments, the aliquoting refers to aliquoting into containers or onto solid supports. The container is selected from the group consisting of vial, tube, package, bag, plate, ampoule, injection device, aluminum film packaging, dressing and capsule.

For example, in particular embodiments, the aliquoting refers to aliquoting into vials/ampoules. Solvent is added to the vial/ampule just before use.

According to some embodiments of the present disclosure, provided is a product derived from *Rhodococcus ruber* cell wall, which is obtained by the preparation method according to present disclosure.

According to some embodiments of the present disclosure, provided is a pharmaceutical composition or a medical device, which comprises a product derived from *Rhodococcus ruber* cell wall obtained by the preparation method according to present disclosure.

According to some embodiments of the present disclosure, provided is an isolated *Rhodococcus ruber* cell wall, which is used for the regulation of adult stem cells. The regulation is selected from one of the following or a combination thereof: promoting the proliferation of stem cells, promoting the growth of stem cells, promoting the differentiation of stem cells, promoting the migration of stem cells, and improving the survival rate of stem cells; the stem cells are selected from the group consisting of adult stem cells, iPSCs and mesenchymal stem cells.

In some embodiments, the mesenchymal stem cells are selected from the group consisting of bone marrow mesenchymal stem cells, adipose-derived mesenchymal stem cells, synovial mesenchymal stem cells, umbilical cord mesenchymal stem cells, umbilical cord blood mesenchymal stem cells, placental mesenchymal stem cells, amniotic mesenchymal stem cells, liver mesenchymal stem cells, muscle mesenchymal stem cells, lung mesenchymal stem cells, pancreatic mesenchymal stem cells and dental pulp mesenchymal stem cells.

According to some embodiments of the present disclosure, provided is a product derived from *Rhodococcus ruber* cell wall, which is used for the regulation of adult stem cells.

According to some embodiments of the present disclosure, provided is a pharmaceutical composition or a medical device, which is used for the regulation of adult stem cells.

According to some embodiments of the present disclosure, provided is a use of the *Rhodococcus ruber* cell wall according to the present disclosure for the regulation of adult stem cells.

Also provided is a use of the *Rhodococcus ruber* cell wall of the present disclosure in the preparation of a medicament/medical device for the regulation of adult stem cells.

According to some embodiments of the present disclosure, provided is a use of the product derived from *Rhodo-*

*coccus ruber* cell wall according to the present disclosure for the regulation of adult stem cells; also provided is a use of the product derived from *Rhodococcus ruber* cell wall of the present disclosure in the preparation of a medicament/medical device for the regulation of adult stem cells.

According to some embodiments of the present disclosure, provided is a use of the pharmaceutical composition according to the present disclosure for the regulation of adult stem cells; also provided is a use of the pharmaceutical composition according to the present disclosure in the preparation of a medicament/medical device for the regulation of adult stem cells.

According to some embodiments of the present disclosure, provided is use of any one selected from the following in the preparation of a medicament (or medical device):

the *Rhodococcus ruber* according to the present disclosure, the isolated *Rhodococcus ruber* cell wall according to the present disclosure, the product derived from *Rhodococcus ruber* cell wall according to the present disclosure, the pharmaceutical composition according to the present disclosure.

In some particular embodiments, the medicament is used for the regulation of adult stem cells.

In some particular embodiments, the medical device (such as dressing, patch, bandage, film, patch, etc.) is used for the regulation of adult stem cells.

According to some embodiments of the present disclosure, also provided is a method for the regulation of adult stem cells, comprising exposing a subject to a therapeutically effective amount (or a prophylactically effective amount) of any one selected from of the following:

the isolated *Rhodococcus ruber* cell wall according to the present disclosure, the product derived from *Rhodococcus ruber* cell wall according to the present disclosure, the pharmaceutical composition according to the present disclosure, the medical device according to the present disclosure.

In some particular embodiments, provided is a method for the regulation of stem cells, comprising a step of exposing the stem cells to a product derived from *Rhodococcus ruber* cell wall.

In some particular embodiments, the ratio of the number of stem cells/the product derived from *Rhodococcus ruber* cell wall is: 1 to 1000 stem cells/1 ng of the product derived from *Rhodococcus ruber* cell wall; preferably 5 to 50 stem cells/1 ng of the product derived from *Rhodococcus ruber* cell wall. For example but not limited to 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 stem cells/1 ng of the product derived from *Rhodococcus ruber* cell wall, and any ranges between them.

In some particular embodiments, provided is a method for promoting wound healing, comprising a step of exposing the wound of a subject to a therapeutically effective amount of mesenchymal stem cells and the product derived from *Rhodococcus ruber* cell wall.

In some embodiments, the ratio of the number of mesenchymal stem cells/the product derived from *Rhodococcus ruber* cell wall is: 1 to 100 stem cells/1 ng of the product derived from *Rhodococcus ruber* cell wall; preferably 5 to 50 stem cells/1 ng of the product derived from *Rhodococcus ruber* cell wall. In some particular embodiments, the wound is a wound related to diabetes.

In some particular embodiments, the medicament (or medical device) is administered to the lesion according to the area and depth of the lesion. For example, but not limited to:

applying a medicament comprising *Rhodococcus ruber* cell wall skeleton; or covering the lesion with a patch (film or gauze) impregnated with *Rhodococcus ruber* cell wall skeleton; or directly administering a lyophilized powder comprising *Rhodococcus ruber* cell wall skeleton to the lesion; or administering an ointment/cream comprising *Rhodococcus ruber* cell wall skeleton to the lesion.

In some particular embodiments, the period of exposure lasts 2 days to 2 months or longer. Specifically speaking, for example 2, 4, 6, 8, 10, 15, 20, 25, 30, 35, 40, 45, 50, 55, 60 days; or for example, mention may be made of 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks or longer. In particular embodiments, the active component is administered to the subject for 3 to 4 weeks.

In some embodiments, the active component is administered at a frequency selected from the following: administering 1 to 3 times per day, 1 to 6 times per two days, 1 to 9 times per three days, 1 to 14 times per week, 1 to 60 times per month. In some embodiments, the active component is administered twice a day, or once a day, or once every two days.

Regarding the amount of each administration, different doses are applied depending on the particular conditions of the subject, usually 1 μg to 1000 μg/unit dose/each administration; specifically speaking, for example 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 μg/unit dose/each administration, and the ranges between any two of the above values.

In some particular embodiments, the exposure is achieved by the following routes, for example but not limited to: oral, mucosal, percutaneous, transdermal, intraperitoneal, puncture, nasal spray, eye drops, suppository and sublingual.

In some particular embodiments, the subject is an animal other than human, for example farm animal, pet, working animal, ornamental animal and production animal.

In particular embodiments, the subject is a human.

In some particular embodiments, the subject is suspected of having, confirmed to have, has suffered from, or is susceptible to the target disease or symptoms thereof.

In some embodiments, provided is a cell culture medium comprising one or a combination selected from the following:

the *Rhodococcus ruber* according to the present disclosure, the isolated *Rhodococcus ruber* cell wall according to the present disclosure, the product derived from *Rhodococcus ruber* cell wall according to the present disclosure, the pharmaceutical composition according to the present disclosure.

In some particular embodiments, provided is a cell culture medium, which further comprises other components well known in the art suitable for culturing stem cells, especially mesenchymal stem cells. When applied to humans, in order to provide safer cells, it is recommended that the culture process be free of xenobiotic animal components; for example using serum-free culture medium.

In some particular embodiments, the skilled person can add cytokines, such as one or a combination of FGF, PDGF, TGF-β, HGF, EGF, CTGF, VEGF, insulin and insulin-like growth factors, to the cell culture medium as needed (for example, to maintain stemness, or to promote differentiation).

In some particular embodiments, the content of FGF (in final concentration) is preferably 0.1 to 100 ng/ml. FGF refers to a growth factor in the fibroblast growth factor family, preferably FGF-1, FGF-2 (bFGF).

In some particular embodiments, the content of PDGF (final concentration) is preferably 0.5 to 100 ng/ml. PDGF refers to a growth factor in the platelet-derived growth factor family, preferably PDGF-BB or PDGF-AB.

In some particular embodiments, the content of TGF-β (final concentration) is preferably 0.5 to 100 ng/ml. TGF-β refers to a growth factor in the transforming growth factor-beta family, preferably TGF-β3.

In some particular embodiments, the content of HGF (final concentration) is preferably 0.1 to 50 ng/ml.

In some particular embodiments, the content of EGF (final concentration) is preferably 0.5 to 200 ng/ml.

In some particular embodiments, provided is a cell culture medium, which further comprises at least one phospholipid, and/or at least one fatty acid.

The phospholipid includes, for example, phosphatidic acid, lysophosphatidic acid, phosphatidyl cyclohexanol, phosphatidyl serine, phosphatidyl ethanolamine, phosphatidyl choline and phosphatidyl glycerol. The total content of phospholipid (final concentration) is preferably 0.1 to 30 μg/ml.

The fatty acid includes, for example, linoleic acid, oleic acid, linolenic acid, arachidonic acid, tetradecanoic acid, palmitoleic acid, palmitic acid, stearic acid, and the like. The total content of fatty acid is preferably $1/1000$ to $1/10$ of the medium.

In some particular embodiments, provided is a cell culture medium, which further comprises cholesterol.

In some particular embodiments, provided is a cell culture medium, which further comprises ascorbic acid.

In some particular embodiments, provided is a cell culture medium, which further comprises an antioxidant. The antioxidant includes, for example, DL-α-tocopheryl acetate (vitamin E).

In some particular embodiments, provided is a cell culture medium, which further comprises transferrin.

In some particular embodiments, provided is a cell culture medium, which further comprises selenate.

In some particular embodiments, provided is a cell culture medium, which further comprises amino acids, nucleotides and trace elements required to maintain cells.

In a particular example, the composition of the present application is added to a known commercially available mesenchymal stem cell culture medium; for example, the commercially available mesenchymal stem cell culture medium is selected from the group consisting of MesenPRO RS™, StemPro® MSC SFM, StemPro® MSC SFM Xeno-Free and StemPro® human adipose-derived stem cell medium.

According to some embodiments, provided is a therapeutic composition comprising:
  mesenchymal stem cells, and
  a product derived from *Rhodococcus ruber* cell wall.

In some embodiments of therapeutic compositions, the ratio of the number of mesenchymal stem cells/the product derived from *Rhodococcus ruber* cell wall is: 1 to 100 stem cells/1 ng of the product derived from *Rhodococcus ruber* cell wall; preferably 5 to 50 stem cells/1 ng of the product derived from *Rhodococcus ruber* cell wall.

In some embodiments of therapeutic compositions, the mesenchymal stem cells are selected from the group consisting of bone marrow mesenchymal stem cells, adipose-derived mesenchymal stem cells, synovial mesenchymal stem cells, umbilical cord mesenchymal stem cells, umbilical cord blood mesenchymal stem cells, placental mesenchymal stem cells, amniotic mesenchymal stem cells, liver mesenchymal stem cells, muscle mesenchymal stem cells, lung mesenchymal stem cells, pancreatic mesenchymal stem cells and dental pulp mesenchymal stem cells.

According to some embodiments, provided is a method for improving stem cell apoptosis, comprising a step of exposing the stem cells to an effective amount of the above-mentioned product derived from *Rhodococcus ruber* cell wall.

According to some embodiments, provided is a method for improving stem cell survival, comprising a step of exposing the stem cells to an effective amount of the above-mentioned product derived from *Rhodococcus ruber* cell wall.

In the context of the present application, the only therapeutic (or prophylactic) active component in the medicament or medical device is a product derived from *Rhodococcus ruber* cell wall, notably comprising *Rhodococcus ruber* components (such as proteins, nucleic acids, lipids, cell wall and components thereof, carbohydrates or metabolites), specifically speaking, a product comprising *Rhodococcus ruber* cell wall, more preferably *Rhodococcus ruber* cell wall skeleton or components thereof.

DETAILED DESCRIPTION OF THE EMBODIMENTS

Figure 1:
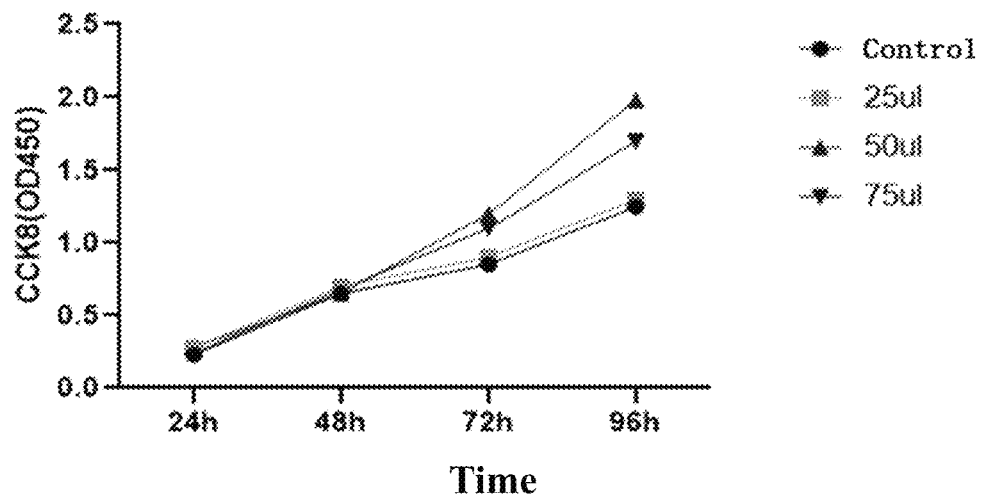
FIG. 1: 10 μg/ml of Composition 1 of the present application was applied to Ad-MSCs for 24 h, 48 h, 72 h and 96 h. Then the absorbance (OD) of the Ad-MSCs at a wavelength of 450 nm was detected by an enzyme-linked immunometric meter using CCK-8.

"Isolation/isolated" refers to the separation of the *Rhodococcus ruber* of the present disclosure from its original growth environment.

The skilled person knows that the cell wall structures of gram-positive bacteria and gram-negative bacteria are different. Specifically speaking, the cell wall of gram-positive bacteria is thicker (usually 20 nm to 80 nm), comprising about 90% peptidoglycan and about 10% teichoic acid (a polymer formed by alcohol and phosphoric acid molecules, usually existing in the form of sugar ester or amino acid ester). The peptidoglycan layer is dense, even as many as 20 layers. However, the cell wall of gram-negative bacteria is much thinner than that of gram-positive bacteria, and the structure is more complex, divided into outer membrane and peptidoglycan layer (usually 2 nm to 3 nm).

The peptidoglycan layer is a unique component of the bacterial cell wall and is a derivative of heteropolysaccharide. Each peptidoglycan monomer comprises 3 moieties; the sugar unit (for example, at least two sugar molecules are connected by glycosidic bonds to form the framework of peptidoglycan), the peptide tail (a short peptide chain formed by linking several amino acids, which is connected to a N-acetylmuramic acid molecule), and the peptide bridge (which crosslinks the adjacent "peptide tails" to form a high-strength network structure). Different bacteria have different peptide bridges, peptide tails and cross-linking manners.

Isolated *Rhodococcus ruber* Cell Wall Skeleton

In the present disclosure, "isolated *Rhodococcus ruber* cell wall" can be interpreted as either a complete cell wall or an incomplete cell wall (for example, disrupted or partially degraded). Under the teaching of the present disclosure, the skilled person will understand that the components exhibiting the desired activity are derived from *Rhodococcus ruber* cell wall (for example, the cell wall itself or components thereof). Therefore, complete cell wall, disrupted cell wall, incompletely degraded product of cell wall, cell wall components, cell wall extracts and other various forms are allowed to be used in clinical applications, which are all encompassed in the scope of the present disclosure.

Cell Wall Skeleton

A component that constitutes the main structure of the cell wall; however, it cannot be interpreted as merely representing the cross-linked network-like entity in the cell wall, and the skilled person understands that other cell wall components adsorbed onto, bound to and carried by the cross-linked network-like entity are not excluded.

*Rhodococcus ruber*

The *Rhodococcus ruber* used in the embodiments of the present disclosure refers to the *Rhodococcus ruber* species of the *Rhodococcus* genus, and is not limited to a particular cell strain.

Non-limiting examples include the TOY7 strain (Agricultural Environment Microbiological Culture Collection, Nanjing Agricultural University), CGMCC No. 4795, DSM43338, CCTCC No. 2012035, CGMCC No. 16640 and CGMCC No. 17431.

Identification of *Rhodococcus ruber*

According to known or future microbial identification techniques, the skilled person can perform taxonomic identification on a strain of bacteria. For example, the available identification techniques include morphology, physiological and biochemical characteristics, 16S rRNA, and the like. The skilled person understands that with the development of science and technology, identification techniques involve different methods. In the earlier period, morphological and biochemical identification methods were mainly used, but the reliability of these methods is not high. After the advent of sequencing technology, the skilled person can identify bacteria strains in a more reliable way. For example, when the DNA sequences of 16S rRNA are identified as having more than 97% (inclusive) of identity, it is determined that the two bacteria belong to the same species (Hua Gougen et al., The taxonomy and application of *Rhodococcus*, Microbiology China, 2003:30 (4)). In terms of *Rhodococcus ruber*, the known strains deposited in international (or national) collection authorities of strains are used as model strains, and the strains to be identified are compared with the model strains.

Dosage Form

The medicament or pharmaceutical composition or active component or product of the present disclosure can be formulated into, but not limited to, the following forms: ointment, cream, plaster, gel, lotion, tincture, liniment, salve, paste, lyophilized powder, aerosol, suppository, patch, suspension, oral solution, buccal tablet and skin care product (cleanser, toning lotion, serum, lotion, cream and mask).

Formulation Unit

The medicament or pharmaceutical composition or active component or product of the present disclosure can be formulated into the form of a formulation unit.

In some embodiments, the unit dose of the medicament (or formulation, or therapeutic agent, or medical device) comprises:

1 μg to 1000 μg of the product derived from *Rhodococcus ruber* cell wall; or

1 μg to 1000 μg of the *Rhodococcus ruber* cell wall; or

1 μg to 1000 μg of the *Rhodococcus ruber* cell wall skeleton.

Particular examples of the unit dose are 1, 2, 5, 10, 15, 20, 25, 30, 40, 50, 55, 56, 57, 58, 59, 60, 61, 62, 63, 65, 66, 67, 68, 69, 70, 80, 90, 100, 150, 200, 250, 300, 350, 400, 450, 500 mg±10%, and the ranges between any two of the above values.

"Administering", "giving", "be provided with" and "treating", when applied to animals, humans, cells, tissues, organs or biological samples, refer to the contact of the medicament or medical device with the animals, humans, cells, tissues, organs or biological samples.

"Treatment" means administrating an internal or external medicament (therapeutic agent, active component or composition) (such as the *Rhodococcus ruber* cell wall or pharmaceutical composition thereof according to the present disclosure) or a medical device to a subject, in order to alleviate (relieve, delay, improve, cure) one or more disease symptoms to a clinically measurable degree in the subject (or population) to be treated, wherein the subject has, is suspected of having, or is susceptible to one or more diseases or symptoms thereof.

The amount of the medicament (therapeutic agent, active component or composition) that can effectively alleviate any disease symptoms is called the therapeutically effective amount. It can vary depending on a variety of factors, such as the disease state, age and body weight of the subject. It should be understood that the medicament (therapeutic agent, active component or composition) may be ineffective in alleviating the target disease or symptoms thereof of a single subject, but is statistically effective for the target disease or symptoms thereof according to any statistical test method known in the art (such as Student t-test, chi-square test and U test according to Mann and Whitney).

The term "optionally" means that the event following this term can happen, but not necessarily happen; it depends on the situation. For example, "optionally, aliquoting" means that the product is allowed to be aliquoted, but is not necessary to be aliquoted; whether the product is aliquoted or not does not affect the realization of the technical effects.

"A", "an", "single" and "the", if not explicitly stated, also involve the plural forms.

The present disclosure is further described below with reference to the examples, preparation examples and test examples. However, these examples, preparation examples and test examples do not limit the scope of the present disclosure. When the particular conditions are not specified, operation should be performed in accordance with the normal conditions and the conditions recommended by the raw material supplier. The reagents without giving particular sources are conventional reagents purchased on the market.

EXAMPLES

Example 1. Source of the Strain

The *Rhodococcus ruber* used in the following examples is the CGMCC No. 17431 strain, which was deposited at China General Microbiological Culture Collection Center (CGMCC, Institute of Microbiology Chinese Academy of Sciences, Yard No. 1(3), West Beichen Road, Chaoyang District, Beijing, China) on Mar. 22, 2019.

The skilled person especially understands that although a particular cell strain is used in the following particular examples, the realization of the technical effects does not depend on the particular cell line, and any species belonging to the *Rhodococcus* genus, *Rhodococcus ruber* species is applicable.

Example 2. Identification of the Strain

1. Visual Observation of the Morphological Characteristics of the Colonies

The strain was cultured on a glycerol agar medium at 30 to 37° C. (specifically 32 to 35° C.) for 12 to 72 (specifically 36 to 60, such as 40 to 50) hours, and the following was observed:
  the colonies plumped up;
  were orange-red in color (slightly different depending on influences of light, the color of the culture medium, etc.);
  the surface was dry and wrinkled, slightly shiny (slightly different depending on differences in culture conditions);
  were fragile to touch;
  the colony size was about 1 mm to 2 mm (slightly different depending on differences in culture conditions).

2. Microscope Observation

The hyphae grew in a branching structure with septate, and formed mycelium (slightly different depending on differences in culture conditions);

Division of the hyphae formed regular short and thick cells (slightly different depending on differences in culture conditions);

After culturing for 4 to 5 days, the bacteria became short rod-shaped or spherical (slightly different depending on differences in culture conditions).

3. Staining Property

The strain was gram stain positive.

4. Biochemical Reactions

The strain was cultured on a glycerol agar slant medium at 30 to 37° C. (specifically 32 to 35° C.) for 12 to 72 (specifically 36 to 60, such as 40 to 50) hours. Then, the following tests were performed on the culture.

4.1 Acid Production from Carbohydrates

TABLE 1

Test of acid production

| | |
|---|---|
| Positive for: | Glycerin, mannitol, sorbitol, D-arabitol, D-fructose and D-glucose; |
| Negative for: | Inositol, inulin, lactose, sucrose, starch, maltose, glycogen, xylitol, gluconate, trehalose, erythritol, melezitose, melibiose, raffinose, cellobiose, amygdalin, gentiobiose, adonol, arbutin, D-arabinose, L-arabinose, α-methyl-D-glucoside, α-methyl-D-mannoside, D-ribose, D-xylose, L-xylose, N-acetyl-glucosamine, D-turbiose, D-lyxose, β-methyl-D-xyloside, D-galactose, D-tagatose, D-fucose, L-fucose, D-mannose, L-sorbose, L-arabinitol, L-rhamnose and 2-keto-gluconate. |

4.2 Enzyme Activity Determination (API ZYM)

TABLE 2

Enzyme activity determination

| | |
|---|---|
| Positive for: | Alkaline phosphatase, lipid esterase (C8), lipase (C14), leucine araminase, valine araminase, cystine araminase, trypsin, chymotrypsin, acid phosphatase, naphthol-AS-B1-phosphohydrolase and α-glucosidase; |
| Negative for: | N-acetyl-glucosaminidase, esterase (C4), β-galactosidase, β-glucuronidase, β-glucosidase, α-galactosidase, α-mannosidase and β-fucosidase. |

4.3 Nitrate Reduction Reaction: Positive, Catalase: Positive, Tyrosinase: Positive, Amylase: Negative, Oxidase: Negative, Gelatin Liquefaction: Negative.

4.4 Sole Carbon Source

TABLE 3

| Carbon source | |
|---|---|
| Biolog Gen II growth experiment: | Positive for: glucuronamide, β-hydroxy-DL butyric acid, D-fructose-6-phosphate, α-D-glucose, D-fructose, D-mannitol, D-arabitol, D-sorbitol, quinic acid, γ-aminobutyric acid, citric acid, L-malic acid, bromosuccinic acid, Tween 40, propionic acid and acetic acid; |
| Biolog Gen III chemical sensitivity experiment: | Sensitive to: dimethylamine tetracycline, sodium tetradecyl sulfate, rifamycin SV, pH 5.0, 8% sodium chloride, lincomycin, fusidic acid, D-serine, vancomycin, tetrazolium violet and tetrazolium blue; Tolerate to: sodium bromate, 1% sodium lactate, pH 6.0, 1%-4% sodium chloride, nalidixic acid, lithium chloride, potassium tellurite, aztreonam and sodium butyrate. |

4.5. 16S rRNA Identification

The 15 strains isolated from the working seed tube and the 10 different strains isolated from the original seed tube were subjected to genome extraction, 16S rRNA amplification and sequencing. Of these 25 strains in total, the 16S rRNA gene identity was 100%.

Further, the neighbor-joining strain phylogenetic tree constructed based on the Kimura2-parameter algorithm showed that the strain was classified as *Rhodococcus ruber*.

PREPARATION EXAMPLES

Preparation Example 1. Culture Methods

1. *Rhodococcus ruber* can be cultured by conventional microbial production methods.
2. The culture method can be solid culture or liquid culture.
3. There are no special requirements on the nutrient sources in the culture medium. The culture medium can contain carbon sources, nitrogen sources and other nutrient sources that are commonly used for microbial culture.

The carbon source can be any carbon source that can be consumed by *Rhodococcus ruber*, for example fructose, glucose, etc.

The nitrogen source can be broth, peptone, ammonium salt, nitrate and other organic or inorganic nitrogen-containing compounds.

For other nutrient sources, some inorganic salts can be added appropriately, for example NaCl and phosphates.

4. There are no strict limitations on the culture conditions (temperature, time, etc.). Those skilled in the art can choose the conditions that maximize the yield based on the preliminary small-scale pilot test data.
5. As an example, the following culture conditions was used to ferment *Rhodococcus ruber*:
    (1) The culture medium composition comprising:
    peptone, broth, sodium chloride, phosphate, glycerin (and, optionally, agar, when in solid culture).
    (2) Parameters of the culture method:
    After the working strain was recovered, it was transferred to a solid culture medium for 3-5 days, and then transferred to liquid culture (30-37° C., maintained for 3-5 days). The fed-batch semi-continuous mode or the batch mode can be used. The pH, bacterial density, dissolved oxygen and carbon source consumption were monitored during culture.

Preparation Example 2. Bacteria Disruption

The bacteria obtained in Preparation Example 1 were collected and the cells were disrupted (for example, but not limited to by sonication). Any appropriate well-known method in the art is also allowed to disrupt the bacteria, such as CN101250490A or CN101323865A.

The disruption state was checked under a microscope. There should be no more than 5 intact bacteria in each visual field. The disruption was deemed as qualified when several (10 to 30) visual fields checked met this standard.

Preparation Example 3. Removal of Nucleic Acids, Lipids, Proteins and Cell Membranes 1. Removal of Nucleic Acids:
The supernatant after disruption was centrifuged. DNase and RNase were added to the obtained precipitate, and nucleic acids were removed according to the operation recommended by the supplier of the enzymes.
2. Removal of Proteins:
Commonly used protease (such as trypsin) was added to the precipitate, and proteins were removed according to the operation recommended by the supplier of the enzyme.
3. Removal of Lipids:
Organic reagents (for example, but not limited to, any one of acetone, ether and ethanol or a combination thereof) were added to the precipitate, and lipids were removed according to conventional operations in the art.
4. Removal of Cell Membranes:
Triton X-100 was added to the precipitate, and the precipitate was collected by centrifugation according to conventional operations in the art, and rinsed with PBS.

It should be understood that among the above steps for removing impurities, those skilled in the art can adjust the order of the steps to make them compatible with each other.

After removing the non-cell wall components, the precipitate was reconstituted in water for injection, and then set aside till use. Optionally, it could be sterilized at 115° C. for 20-30 minutes as the stock solution of the cell wall skeleton (mainly comprising the cell wall skeleton and components thereof).

Preparation Example 4. Preparation Methods of the Pharmaceutical Compositions

1. Liquid Composition
An excipient (such as dextran 40, mannitol or trehalose) was added to the product obtained in Preparation Example 3. The resulting product was referred to as the pharmaceutical composition after filling into aliquots.

TABLE 4

| Composition | Capacity of each vial | Components and amount |
|---|---|---|
| The pharmaceutical composition can be formulated into various forms | | |
| Composition 1 | 2 ml | Active component 60 µg Dextran 40 15 mg |
| Composition 2 | 2 ml | Active component 60 µg Dextran 40 12 mg |
| Composition 3 | 2 ml | Active component 120 µg Dextran 40 36 mg |
| Composition 4 | 2 ml | Active component 60 µg Trehalose 12 mg |
| Composition 5 | 2 ml | Active component 120 µg Trehalose 36 mg |
| Composition 6 | 2 ml | Active component 120 µg Mannitol 36 mg |
| Composition 7 | 2 ml | Active component 60 µg Mannitol 12 mg |

2. Powder Compositions

The pharmaceutical compositions of item 1 were lyophilized to prepare lyophilized powders (numbered as lyophilized powder Composition 1 to lyophilized powder Composition 7, respectively).

3. Quality Inspection (Lyophilized Powder Composition 1 was Taken as an Example)

TABLE 5

| Quality inspection items | |
|---|---|
| Appearance | White unconsolidated solid or powder |
| Water content | ≤6% |
| Solubility | The product was deemed as qualified if it dissolved within 1 min when 2.0 ml of NaCl injection was added; |
| Residual amount of proteins | 0.4 µg/vial (criteria: ≤9.0 µg/vial) |
| Residual amount of RNA | 0.8% (criteria: not more than 5%) |
| Residual amount of DNA | 0.9% (criteria: not more than 5%) |
| Residual amount of Triton X-100 | Undetectable (criteria: not more than 5%) |
| Residual amount of lipids | 3.8% (criteria: not more than 5%) |
| Phagocytosis rate | 75% (criteria: ≥40%) |
| Phagocytic index | 1.05 (criteria: ≥0.50) |
| Abnormal toxicity in mice | All the mice should survive and have no abnormal reactions during the observation period. The composition was deemed as qualified if the body weight of each mouse increased at the due date |
| Abnormal toxicity in guinea pigs | All the guinea pigs should survive and have no abnormal reactions during the observation period. The composition was deemed as qualified if the body weight of each guinea pig increased at the due date |

Test Examples

Materials and Methods

1. Isolation, Culture and Passage of Human Ad-MSCs

Adipose tissue samples were obtained from liposuction aspirate of subjects (age range 25-35 years) and Ad-MSCs were isolated and cultured. Subjects were chosen from plastic surgery patients in the Affiliated Hospital of Xuzhou Medical University. The experiment were approved by the ethics committee and informed consent of the patients.

The obtained fresh adipose tissue extract was digested with 0.25% trypsin-EDTA, filtered, and centrifuged to retain the cell pellet. DMEM (Invitrogen) culture medium containing 10% fetal bovine serum (FBS. Gibco) and 1% penicillin/streptomycin was added. The cell culture dish was placed in a 37° C. 5% $CO_2$ incubator to culture the cells. After that the culture medium was changed every 2-3 days after washing the cells with PBS. The cells were passaged when growing to 80%.

2. Determination of Cell Viability

Ad-MSCs in logarithmic growth phase were seeded in a 96-well plate at $4×10^3$ cells/well; DMEM+10% fetal bovine serum+1% penicillin/streptomycin was used for co-culture; the composition of the present application (Composition 1) was dissolved and diluted to 10 µg/ml with PBS buffer. After the Ad-MSCs adhered to the wall, for each sample to be tested, the experiment was divided into four groups: control, 25 µl, 50 µl and 75 µl. After 24 h, 48 h, 72 h or 96 h, 10 µL of CCK-8 reagent was added to each well, and incubated for 2 h. Then the absorbance of each well at a wavelength of 450 nm was detected by an enzyme-linked immunometric meter. The cell growth curve was plotted with the culture time as the horizontal axis and the cell number (absorbance) as the vertical axis.

3. EdU Incorporation Experiment

EdU incorporation assay was performed by using CellLight EdU 567 in vitro imaging kit (RiboBio). Ad-MSCs at the logarithmic growth phase were seeded in a 96-well plate at $4×10^3$ cells/well, 10 µg/ml, 50 µl of the composition of the present application was applied onto the Ad-MSCs. 100 µl of EdU medium was added to each well after 72 h or 96 h and incubated for two hours, and the wells were washed with PBS 1-2 times. 4% paraformaldehyde fixative was added to each well and the plate was incubated at room temperature for 30 min. Then 2 mg/ml glycine solution was added and the plate was shaken on a shaker for 5 minutes. After washing with PBS, osmotic agent was added, the plate was shaken on a shaker for 10 min and washed with PBS. Apollo staining reaction solution was added and the plate was incubated at room temperature in the dark for 30 minutes. The staining reaction solution was discarded. Penetrant (0.5% TritonX-100 in PBS) was added and the plate was shaken on a shaker 2-3 times. 10 minutes each time, and the penetrant was discarded. The plate was washed with PBS again and Hoechest 33342 reaction solution was added. The plate was incubated at room temperature in the dark for 30 minutes, and the reaction solution was discarded. After washing 1-3 times with PBS, positive cells were observed by fluorescence microscopy.

4. Detection of Apoptosis 4.1 Flow Cytometry:

When Ad-MSCs reached 80% confluence, they were seeded at a density of 1×10+ cells/well in a 6-well plate. The experiment was divided into four groups. After the cells adhered to the wall, 100 μl of 50% sucrose was added to each experimental group to induce apoptosis of Ad-MSCs; and 100 μl or 250 μl of the composition of the present application at 10 μg/ml was respectively added to two experimental groups among these groups. After 48 h and 72 h. the supernatant of each group of cells was collected in flow tubes. The adherent cells were digested with EDTA-free trypsin and collected into flow tubes of the same group. The tubes were centrifuged at 2000 rpm for 5 min. washed twice with PBS buffer, shaken and mixed well. 500 μl of binding buffer (Annexin V-FITC apoptosis detection kit. Shanghai Beyotime Biotechnology Co., Ltd.), 5 μl of FITC and 5 μl of PI were successively added to each tube. The tubes were shaken and mixed well and incubated in the dark at 4° C. for 5-15 min. The results were detected and analyzed by flow cytometry (BD Biosciences).

4.2 TUNEL Method:

Several 18 mm×18 mm coverslips were sterilized by soaking in 75% ethanol. When using, the coverslips were placed in a 6-well plate and rinsed with PBS buffer several times until the ethanol residue was completely removed. Ad-MSCs were cultured in a 6-well plate at a cell density of $1 \times 10^4$ cells per well. The experimental grouping was the same as that of flow cytometry. The cells were washed 3 times with PBS buffer and fixed in 4% paraformaldehyde at room temperature for 30 min; washed 3 times with PBS buffer and incubated with 0.1% TritionX-100 at 2° C.-8° C. for 10 min; washed 3 times with PBS buffer. 500 μl of TUNEL reaction solution (TUNEL apoptosis kit. Roche) was prepared. 50 μl of enzyme solution and 450 μl of labeling solution were mixed to prepare reagent A. 50 μl of reagent A was added to the negative control group, which was placed in a 37° C. incubator in the dark for 60 min. DNase I was added to the positive control group, which was incubated at room temperature for 10 min. The cells were washed 3 times with PBS buffer and 50 μl/well of TUNEL reaction mixture was added. The cells were incubated in a 37° C. incubator in the dark for 60 min and washed 3 times with PBS buffer. 50 μl/well of DAPI staining solution was added and the cells were incubated at room temperature for 3 min. The samples were photographed under a fluorescence microscope for analysis, and the wavelength range of detection light was 570-620 nm (maximum wavelength 580 nm).

5. Western Blot Analysis

The treated cells were collected. 300 μl of cell lysis mixture (dissolve PIPA cell lysis solution on ice, add PMSF at a ratio of 100:1) was added to each dish and then placed on ice. The cells were fully lysed and adherent cells were scraped. The mixture was centrifuged in a Centrifuge-5810R refrigerated high-speed centrifuge at 4° C. 12.000 rpm for 20 min and the supernatant was collected.

The cell extracts were separated on SDS-polyacrylamide gels. Then the proteins were transferred to nitrocellulose membranes and incubated with the following antibodies: rabbit-anti-human caspase-3 monoclonal antibody (1:400; CST. USA), rabbit-anti-human Bax monoclonal antibody (1:400; CST. USA). After incubation with the primary antibody, the membranes were washed for 5 min×3 times and incubated with diluted secondary antibody (1:10000) at room temperature in the dark for 2 h. The secondary antibody was discarded and the membranes were washed for 5 min×3 times. Equal amounts of ECL luminescent solution A and B were pipetted respectively and mixed well to prepare the ECL working solution. The ECL working solution was evenly dropped on the membranes. The membranes were put into a TANON gel imager for exposure and development, photographed, and analyzed by ImageJ software.

6. Establishment of Diabetic Wound Animal Model

The experimental animals were 4-week-old BALB/c athymic nude mice. SPF grade. All animal studies were approved by the Animal Care and Use Committee. The experimental mice were kept in SPF grade animal room. Mice were fasted for 12 h before model establishment, weighed and recorded. Diabetic mice were induced by intraperitoneal injection of 2% STZ (Sigma) at a dose of 150 mg/kg.

Blood glucose was measured on day 7 after injection. Blood was collected through tail vein, and the blood glucose concentration of the mice was measured with a blood glucose meter and recorded. From day 7, the blood glucose concentration of the mice was greater than 16.7 mmol/L and the typical symptoms of diabetes "polydipsia, polyphagia, polyuria and weight loss" were developed, which was regarded as successful model establishment.

The experimental animals were divided into 3 groups (5 animals in each group):

Blank control group.

Ad-MSC group.

The composition of the present application+Ad-MSC group.

Once the diabetic mouse model was successfully established, the mice were anesthetized and wounds with a diameter of 1.5 cm were prepared. The pretreated Ad-MSCs were injected into the skin of mice in each group by multi-point intradermal injection, with six points on each wound and 0.1 ml of cells injected at each point. The wound surface was covered with sterile gauze, and feeding and observation were continued. The survival of cells in the wound and the skin healing of mice were observed by using LB983 in vivo imaging system.

7. Staining with CM-Dil Live Cell Stain

Ad-MSCs were labeled with CM-Dil before injection. According to the method recommended by the supplier. CM-Dil live cell stain was added to the cells and incubated for 30 minutes. The supernatant was discarded after centrifugation and the cells were washed 3 times with PBS buffer. Finally, an appropriate amount of PBS was added and mixed well, and the labeled Ad-MSCs were placed in an ice box for later use.

8. Tissue Immunofluorescence Staining

The tissue paraffin sections were dewaxed and incubated with 3% $H_2O_2$ at room temperature for 5-10 min to eliminate endogenous peroxidase activity. The sections were rinsed with distilled water, soaked twice in PBS for 5 min each time, and blocked with 10% normal goat serum (diluted in PBS) at room temperature for 10 min. The blocking solution was discarded without washing the sections. CD31 primary antibody (dilution ratio 1:300) working solution was added dropwise and incubated overnight. The sections were rinsed 3 times with PBS for 5 min each time. An appropriate amount of biotin-labeled fluorescent secondary antibody working solution (dilution ratio 1:400) was added dropwise in the dark. The sections were incubated at 37° C. in the dark for 1 h and rinsed 3 times with PBS for 5 min each time. An appropriate amount of DAPI staining solution was added dropwise. The sections were incubated at room temperature in the dark for 3 min and rinsed 3 times with PBS for 5 min each time. Finally, anti-fluorescence quenching sealing solution was added dropwise to each section. The sections were covered with coverslips, fixed, and stored in the dark.

9. Statistical Analysis

Statistical analysis was performed by using SPSS software (SPSS 16.0). The experimental results were represented as mean±SD. The comparison between two groups was performed by independent samples t-test, and the comparison of means among multiple groups was performed by one-way ANOVA, $\alpha=0.05$ was the level of significance, and the difference with $P<0.05$ was considered to be statistically significant.

Test Example 1. Identification of Morphology, Surface Markers and Induced Differentiation Ability of Human Ad-MSCs The collagenase digestion method was used. Primary Ad-MSCs extracted from adipose tissue extracts were seeded in cell culture dishes and passaged when they reached 80% confluence. The proliferation rate of the cells increased significantly after passage. The cells were uniform in terms of morphology and spindle-shaped. Well-grown Ad-MSCs of the P3 generation were used for adipogenic differentiation and osteogenic differentiation, respectively. Observation of the cells stained with oil red after 2 weeks under a microscope showed obvious presence of red lipid droplets of different sizes in the cells; observation of the cells stained with alizarin S stain showed obvious deposition of red calcium nodules. This indicated that the isolated and extracted cells had the characteristics of stem cell differentiation potential.

6 different cell surface markers were detected by flow cytometry. The results showed that the cells were positive for CD105. CD90 and CD44; negative for CD31. CD34 and CD106. These results were consistent with the characteristics of the Ad-MSC immunophenotype.

Test Example 2. Effects of the Composition of the Present Application on the Activity and Proliferation of Ad-MSCs In order to detect the effect of the composition of the present application on the activity of Ad-MSCs. Composition 1 of the present application was applied to Ad-MSCs for 24 h, 48 h, 72 h and 96 h. Then the absorbance of the stem cells at a wavelength of 450 nm was detected by an enzyme-linked immunometric meter using CCK-8 reagent. The results showed that the viability of Ad-MSCs was significantly enhanced at 72 h and 96 h after introducing the composition of the present application into the stem cells, at a concentration of 10 µg/ml and a volume of 50 µl (FIG. 1).

Figure 2:
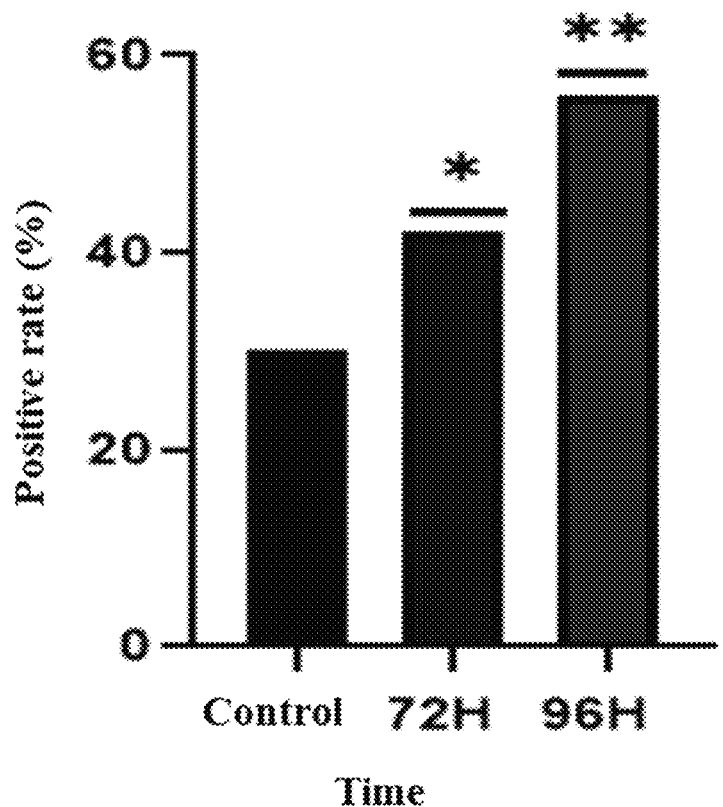
FIG. 2: Ad-MSCs were treated with 10 μg/ml, 50 μl of Composition 1 of the present application for 72 h and 96 h. Then the EdU incorporation analysis was performed by using EdU kits, the cell proliferation rate of each group was statistically analyzed, and the experiment was repeated for 3 times. The data are represented by bar graphs as mean±SD (*$P<0.05$, **$P<0.01$, vs. control).

In order to verify the effect of the composition of the present application on the proliferation of Ad-MSCs, 10 µg/ml, 50 µl of the composition of the present application was applied to stem cells. The incorporation of EdU was analyzed by using the EdU kit after 72 h and 96 h. respectively. The positive cells were observed by fluorescence microscopy. The results showed that the composition of the present application could increase the proliferation rate of Ad-MSCs (FIG. 2).

Test Example 3. The Composition of the Present Application Inhibits the High Glucose-Induced Apoptosis of Ad-MSCs High glucose was added to Ad-MSCs to induce apoptosis. After treating the cells with different concentrations of Composition 1 of the present application for 48 h and 72 h. respectively, apoptosis was detected by using FITC-PI flow cytometry apoptosis detection kit.

Figure 3A:
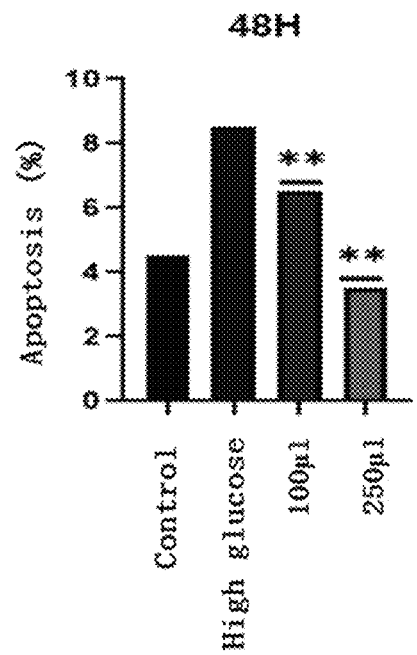
FIG. 3A to FIG. 3B: The apoptosis rate of stem cells in blank control group, high glucose group, and the group treated with the composition of the present application at 48 h and 72 h was detected by flow cytometry. The experiment was repeated for 3 times. The data are represented by bar graphs as mean±SD (**$P<0.01$, vs. high glucose).
Figure 3B:
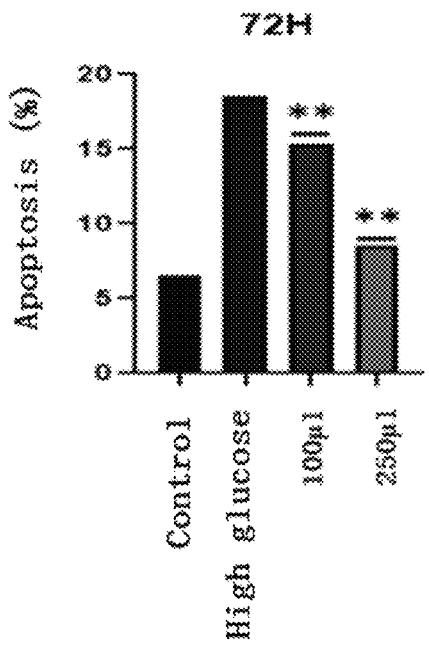

The results showed that the composition of the present application could inhibit the high glucose-induced apoptosis of stem cells (FIG. 3A. FIG. 3B).

Test Example 4. Detection of Expression Levels of Apoptosis Marker Proteins

Figure 4A:
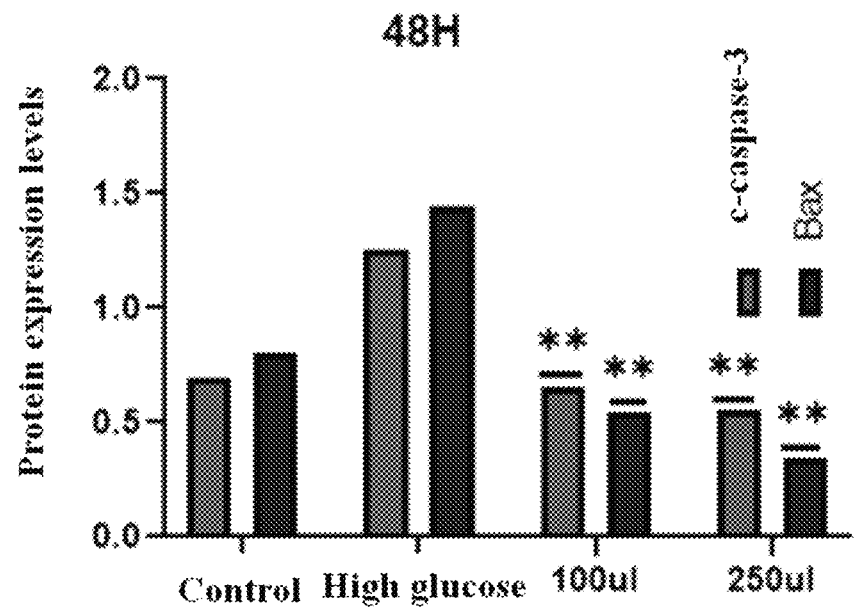
FIG. 4A and FIG. 4B: High glucose was added to the cells to induce apoptosis. Western blotting was performed to detect the protein expression levels of c-caspase-3 and Bax. The experiment was repeated for 3 times. The data are represented by bar graphs as mean±SD (*$P<0.05$, **$P<0.01$, vs. high glucose).
Figure 4B:
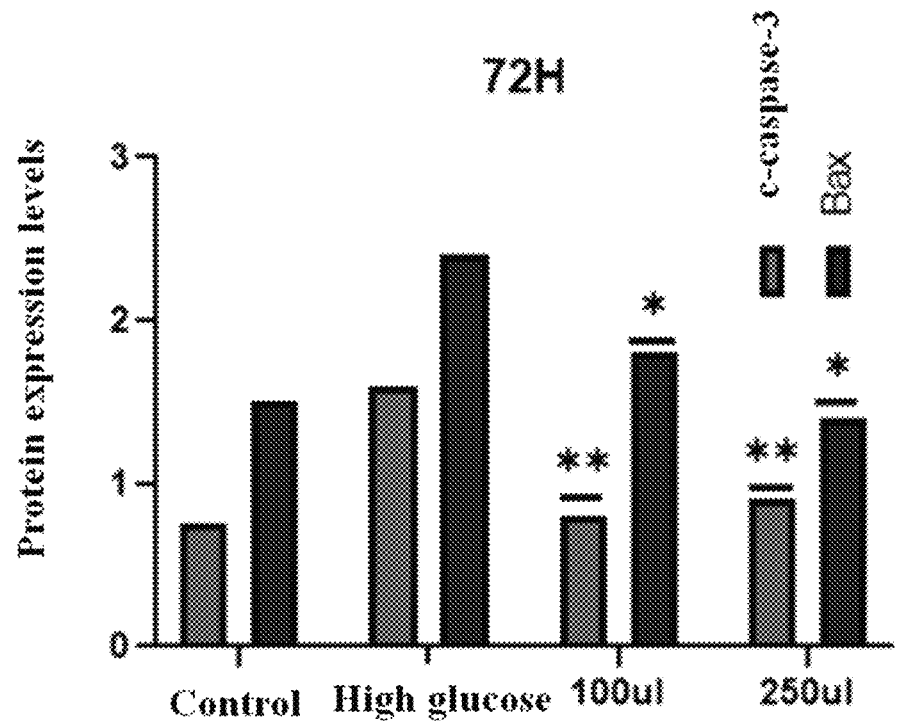

High glucose was added to the cells to induce apoptosis. The cells were treated with different concentrations of the composition of the present application for 48 h and 72 h, and cellular proteins were extracted. The protein expression levels of c-caspase-3 and Bax (two major apoptotic markers) were detected by Western blotting experiments, and β-actin was used as an internal reference. The results showed that the expression levels of c-caspase-3 and Bax proteins were decreased after treatment with the composition of the present application (FIG. 4A. FIG. 4B).

Test Example 5. The Composition of the Present Application Improves the Survival Rate of Ad-MSCs and Accelerates Wound Healing in Nude Mice In order to further explore the effect of the composition of the present application on Ad-MSCs in diabetic wound healing, a wound model simulating the mechanism of wound repair in human skin was established in diabetic nude mice.

After the successful establishment of diabetic mouse model, the mice were anesthetized and wounds with a diameter of 1.5 cm were prepared. The pretreated cells labeled with fluorescent dye CM-Dil were injected into the wound skin of mice in treatment group by intradermal injection. The survival of cells was observed by using LB983 in vivo imaging system.

Figure 5A:
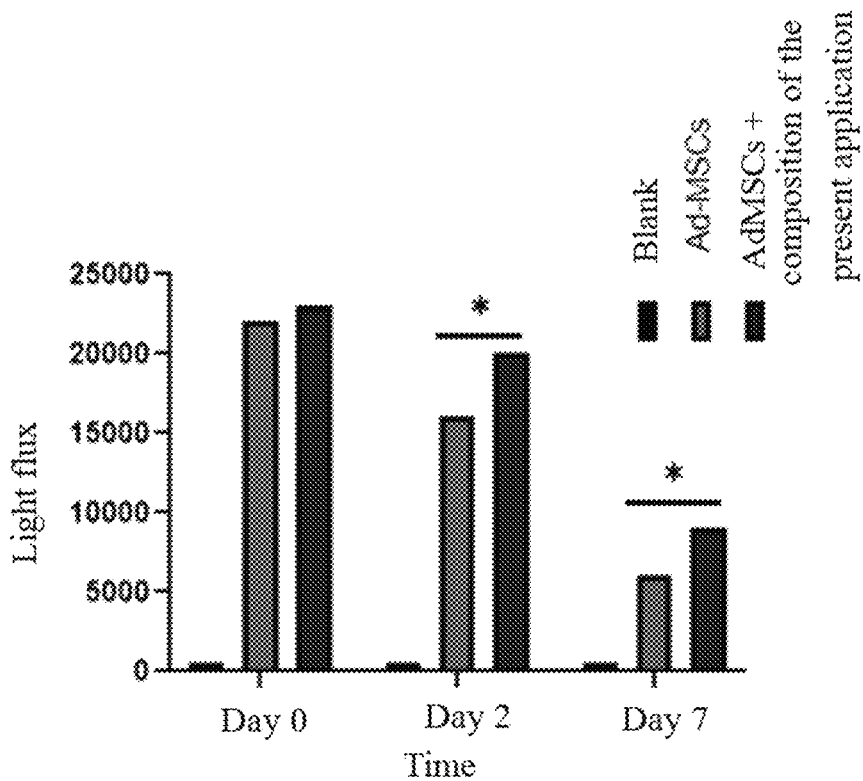
FIG. 5A: Cells were inoculated into the wounds of diabetic mice. Then the survival rate of Ad-MSCs in each group was observed according to the cells labeled with the fluorescent dye CM-Dil on day 0, day 2 and day 7. The fluorescence flux results of CM-Dil-labeled cells were statistically analyzed.
Figure 5B:
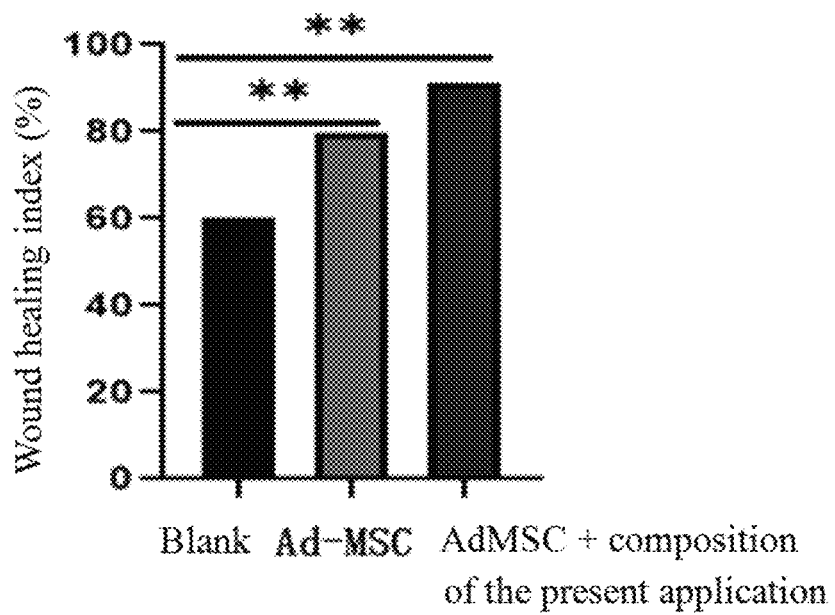
FIG. 5B: Wound healing rate in each group was measured and calculated (*$P<0.05$, **$<0.01$, vs. blank).

The results showed that the Ad-MSCs in the group treated with the composition of the present application had a higher survival rate than the group using Ad-MSCs alone (FIG. 5A). The wound healing process of diabetic mice treated with Ad-MSCs was also evaluated for 14 days. Compared with the blank group, the wounds of the mice treated with Ad-MSCs healed well, while the group treated with the composition of the present application healed better, with accelerated wound healing (FIG. 5B) and an increased wound healing rate (Table 6).

TABLE 6

Wound healing on day 14 after operation
(mean ± SD, n = 3)

| Group | Wound healing rate (%) |
|---|---|
| Blank | 58.5 ± 1.8 |
| Ad-MSC | 78.0 ± 1.5** |
| Ad-MSC + the composition of the present application | 90.5 ± 0.8** |

**$P < 0.01$, vs. blank.

There are many reasons for the formation of diabetic refractory wounds, for example, the absence of cellular and molecular signals required for normal wound healing process. In addition, peripheral neuropathy, peripheral circulation damage and disturbance of protease balance are all important factors for refractory healing of diabetic wounds (Rathur H M et al., The diabetic foot. Clin Dermatol. 2007; 25(1): 109-120). On the other hand, the abnormal vascular microenvironment under high glucose conditions can lead to abnormal cell growth environment, and ultimately damage the vascular reconstruction in the trauma area (Guo W Y et al., Acceleration of diabetic wood healing by low-dose radiation is associated with peripheral mobilization of bone marrow stem cells. Radiat Res. 2010; 174(4): 467-479). In addition, the reduced number of fibroblasts, increased glycosylated proteins, abnormal growth factor expression, delayed inflammatory process, and accumulation of glycosylated end products in traumatized tissues under diabetic high glucose conditions all affect the migration and function of bone marrow-derived cells (Fiorina P et al., The mobilization and effect of endogenous bone marrow progenitor cells diabetic wound healing. Cell Transplant. 2010; 19(11): 1369-1381).

Ad-MSCs are a kind of stem cells with multi-directional differentiation potential extracted from adipose tissue (Kato Y et al., Creation and transplantation of an adipose-derived stem cell (ASC) sheet in a diabetic wound-healing model. Jove-J Vis Exp. 2017; 12(6): 1-10). Ad-MSCs can migrate to damaged sites through differentiation potential, repair damaged skin with differentiated cells, and secrete a variety of growth factors (Rehman J et al., Secretion of angiogenic and anti-apoptotic factors by human adipose stromal cells. Circulation. 2004; 109: 1292-8). They accelerate wound angiogenesis and promote wound healing (Ebrahimian T G et al., Cell therapy based on adipose tissue-derived stromal cells promotes physiological and pathological wound healing. Arterioscler Thromb Vasc Biol. 2009; 29(4): 503-510).

Some scholars have also found that Ad-MSCs can differentiate into fibroblasts, showing not only morphological similarity, but also the ability to express fibroblast surface proteins, including vimentin and fibronectin (Kim W S et al., Wound healing effect of adipose-derived stem cells: a critical role of secretory factors on human dermal fibroblasts. J Dermatol Sci. 2007; 48:15-24). Meanwhile, Ad-MSCs can also be directly transformed into fibroblasts and keratinocytes for wound repair (Unnikrishnan S et al., Constitution of fibrin-based niche for in vitro differentiation of adipose-derived mesenchymal stem cells to keratinocytes. Biores Open Access. 2014; 3(6): 339-347). However, previous studies have found that most Ad-MSCs undergo apoptosis when injected into wounds of diabetic mice, resulting in delayed wound healing. Ad-MSCs cultured under high glucose conditions undergo apoptosis in a time-dependent manner (Li Q et al., Stromal cell-derived factor-1 promotes human adipose tissue-derived stem cell survival and chronic wound healing. Exp Ther Med. 2016; 12:45-50).

In the test examples, the effects of the composition of present application on in vitro activity and proliferation ability of Ad-MSCs were detected by CCK-8 and EdU. The results showed that the composition of the present application could improve the activity and proliferation ability of Ad-MSCs. Apoptosis of cells was detected by flow cytometry, and it was found that the composition of the present application could inhibit the high glucose-induced apoptosis of Ad-MSCs in a time- and concentration-dependent manner.

The effect of the composition of the present application on the survival rate of Ad-MSCs was tested in vivo in animals, and the results showed that the survival rate of Ad-MSCs treated with the composition of the present application was higher than that treated with Ad-MSCs alone, and the wound healing speed was faster.

What is claimed:

1. A method of regulating mesenchymal stem cells comprising exposing the stem cells to a product derived from *Rhodococcus ruber* cell wall; wherein the ratio of the number of stem cells to the product derived from *Rhodococcus ruber* cell wall is 1 to 100 stem cells per 1 ng of the product derived from *Rhodococcus ruber* cell wall.

2. The method of claim 1, wherein the ratio is 5 to 50 stem cells per 1 ng of the product derived from *Rhodococcus ruber* cell wall; and the regulation is selected from one of the following: promoting the proliferation of mesenchymal stem cells, promoting the growth of mesenchymal stem cells, improving the survival rate of mesenchymal stem cells, and a combination thereof.

3. The method of claim 1, wherein the mesenchymal stem cells selected from the group consisting of: bone marrow mesenchymal stem cells, adipose-derived mesenchymal stem cells, synovial mesenchymal stem cells, umbilical cord mesenchymal stem cells, umbilical cord blood mesenchymal stem cells, placental mesenchymal stem cells, amniotic mesenchymal stem cells, liver mesenchymal stem cells, muscle mesenchymal stem cells, lung mesenchymal stem cells, pancreatic mesenchymal stem cells, and dental pulp mesenchymal stem cells.

4. The method of claim 1, wherein the mesenchymal stem cells are adipose-derived mesenchymal stem cells.

5. The method according to claim 1, wherein the product derived from *Rhodococcus ruber* cell wall is obtained by the following method comprising the following steps:
   1) Providing a *Rhodococcus ruber*;
   2) Disrupting the *Rhodococcus ruber* to obtain a disrupted product;
   3.1) optionally, removing lipids from the disrupted product;
   3.2) optionally, removing nucleic acids from the disrupted product;
   3.3) optionally, removing proteins from the disrupted product;
   3.4) obtaining a product derived from *Rhodococcus ruber* cell wall;
   4) Optionally, removing water from the product derived from *Rhodococcus ruber* cell wall, preferably lyophilizing the product derived from *Rhodococcus ruber* cell wall;
   5) Optionally, aliquoting;
   wherein, steps 3.1), 3.2) and 3.3) are interchangeable in order or performed in parallel; step 4) and step 5) are interchangeable in order.

6. The method of claim 1, wherein the *Rhodococcus ruber* is CGMCC No. 17431 deposited on Mar. 22, 2019.

7. A cell culture medium comprising a product derived from *Rhodococcus ruber* cell wall and a mesenchymal stem cell, wherein the product derived from *Rhodococcus ruber* cell wall is *Rhodococcus ruber* cell wall or a component thereof.

8. The cell culture medium according to claim 7, wherein the product derived from *Rhodococcus ruber* cell wall is obtained by the following method comprising the following steps:

1) Providing a *Rhodococcus ruber*;
2) Disrupting the *Rhodococcus ruber* to obtain a disrupted product;
3.1) optionally, removing lipids from the disrupted product;
3.2) optionally, removing nucleic acids from the disrupted product;
3.3) optionally, removing proteins from the disrupted product;
3.4) obtaining a product derived from *Rhodococcus ruber* cell wall;
4) Optionally, removing water from the product derived from *Rhodococcus ruber* cell wall, preferably lyophilizing the product derived from *Rhodococcus ruber* cell wall;
5) Optionally, aliquoting;
wherein, steps 3.1), 3.2) and 3.3) are interchangeable in order or performed in parallel; step 4) and step 5) are interchangeable in order.

9. The cell culture medium according to claim 7, wherein the *Rhodococcus ruber* is CGMCC No. 17431 deposited on Mar. 22, 2019.

10. A method for promoting wound healing, comprising exposing a subject having a wound to a therapeutically effective amount of stem cells and a product derived from *Rhodococcus ruber* cell wall, wherein the stem cells are selected from the group consisting of mesenchymal stem cells and the ratio of the number of stem cells to the product derived from *Rhodococcus ruber* cell wall is 1 to 100 stem cells per 1 ng of the product derived from *Rhodococcus ruber* cell wall.

11. The method of claim 10, wherein the wound is a diabetes-related wound and the ratio is 5 to 50 stem cells per 1 ng of the product derived from *Rhodococcus ruber* cell wall; and the regulation is selected from one of the following: promoting the differentiation of stem cells, promoting the migration of stem cells, improving the survival rate of stem cells, and a combination thereof.

12. The method of claim 10, wherein the stem cells are selected from the group consisting of: mesenchymal stem cells; and the *Rhodococcus ruber* is CGMCC No. 17431 deposited on Mar. 22, 2019.

13. The method of claim 12, wherein the stem cells are mesenchymal stem cells selected from the group consisting of: bone marrow mesenchymal stem cells, adipose-derived mesenchymal stem cells, synovial mesenchymal stem cells, umbilical cord mesenchymal stem cells, umbilical cord blood mesenchymal stem cells, placental mesenchymal stem cells, amniotic mesenchymal stem cells, liver mesenchymal stem cells, muscle mesenchymal stem cells, lung mesenchymal stem cells, pancreatic mesenchymal stem cells and dental pulp mesenchymal stem cells.

14. The method of claim 10, wherein the mesenchymal stem cells are adipose-derived mesenchymal stem cells.

15. A pharmaceutical composition comprising:
(i) stem cells, and
(ii) a product derived from *Rhodococcus ruber* cell wall, wherein the stem cells are selected from the group consisting of mesenchymal stem cells; and the ratio of the number of stem cells to the product derived from *Rhodococcus ruber* cell wall is: 1 to 100 stem cells to 1 ng of the product derived from *Rhodococcus ruber* cell wall.

16. The pharmaceutical composition of claim 15, wherein the ratio is 5 to 50 stem cells per 1ng of the product derived from *Rhodococcus ruber* cell wall; and the regulation is selected from one of the following: promoting the proliferation of stem cells, promoting the growth of stem cells, improving the survival rate of stem cells, and a combination thereof.

17. The pharmaceutical composition of claim 15, wherein the stem cells are mesenchymal stem cells selected from the group consisting of: bone marrow mesenchymal stem cells, adipose-derived mesenchymal stem cells, synovial mesenchymal stem cells, umbilical cord mesenchymal stem cells, umbilical cord blood mesenchymal stem cells, placental mesenchymal stem cells, amniotic mesenchymal stem cells, liver mesenchymal stem cells, muscle mesenchymal stem cells, lung mesenchymal stem cells, pancreatic mesenchymal stem cells and dental pulp mesenchymal stem cells; and the product derived from *Rhodococcus ruber* cell wall is *Rhodococcus ruber* cell wall or a component thereof from *Rhodococcus ruber* deposited m CGMCC under the number CGMCC No. 17431 on Mar. 22, 2019.

* * * * *